United States Patent

Nishiyama et al.

[11] 4,235,621
[45] Nov. 25, 1980

[54] 2-SUBSTITUTED PHENOXY-3-CHLORO-5-TRIFLUOROMETHYL PYRIDINE USEFUL AS A HERBICIDE

[75] Inventors: Ryuzo Nishiyama, Takatsuki; Kanichi Fujikawa, Moriyama; Takahiro Haga, Kusatsu; Tadaaki Toki, Moriyama; Terumasa Komyoji; Nobuyuki Sakashita, both of Kusatsu; Kazuyuki Maeda, Hikone, all of Japan

[73] Assignee: Ishihara Sangyo Kaisha Ltd., Osaka, Japan

[21] Appl. No.: 43,611

[22] Filed: May 30, 1979

[30] Foreign Application Priority Data

Jun. 9, 1978 [JP] Japan .................... 53/68848

[51] Int. Cl.$^3$ .................................... C07D 213/64
[52] U.S. Cl. ............................ 71/94; 546/300; 546/302; 546/345
[58] Field of Search ................ 71/94; 546/300, 302

[56] References Cited

U.S. PATENT DOCUMENTS

| | | | |
|---|---|---|---|
| 3,429,689 | 2/1969 | Duerr et al. | 546/302 |
| 3,609,158 | 9/1971 | Torba | 546/302 |
| 4,046,553 | 9/1977 | Takahashi et al. | 546/302 |
| 4,152,328 | 5/1979 | Nishiyama et al. | 71/94 |

Primary Examiner—Donald G. Daus
Assistant Examiner—James H. Turnipseed
Attorney, Agent, or Firm—Oblon, Fisher, Spivak, McClelland & Maier

[57] ABSTRACT

2-Substituted phenoxy-3-chloro-5-trifluoromethyl pyridine having the formula (I):

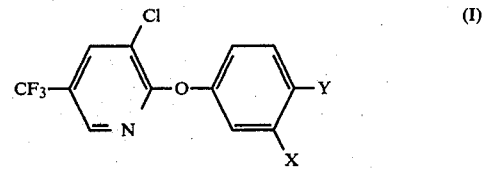

wherein X is a hydrogen atom; a $(C_1-C_4)$alkyl group; a $(C_1-C_4)$alkoxy group; a $-COOR_1$ group wherein $R_1$ is a hydrogen atom, a cation or a $(C_1-C_4)$alkyl group; or an

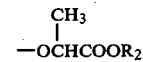

group wherein $R_2$ is a hydrogen atom, a cation, a $(C_1-C_4)$alkyl group or a benzyl group; and Y is a halogen atom, a nitro group or a cyano group, useful as a herbicide.

20 Claims, No Drawings

2-SUBSTITUTED PHENOXY-3-CHLORO-5-TRIFLUOROMETHYL PYRIDINE USEFUL AS A HERBICIDE

BACKGROUND OF THE INVENTION

1. Field of the Invention

This invention relates to a novel 2-substituted phenoxy-3-chloro-5-trifluoromethyl pyridine, and a herbicidal composition containing the same.

SUMMARY OF THE INVENTION

The present invention provides a 2-substituted phenoxy-3-chloro-5-trifluoromethyl pyridine having the formula (I):

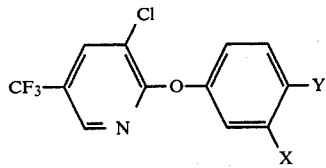

wherein X is a hydrogen atom; a ($C_1$-$C_4$) alkyl group; a ($C_1$-$C_4$) alkoxy group; a -$COOR_1$ group wherein $R_1$ is a hydrogen atom, a cation or a ($C_1$-$C_4$) alkyl group; or an

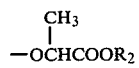

group wherein $R_2$ is a hydrogen atom, a cation, a ($C_1$-$C_4$) alkyl group or a benzyl group; and Y is a halogen atom, a nitro group or a cyano group.

The invention further provides a herbicidal composition comprising a herbicidally effective amount of at least one compound of the above general formula (I) and agriculturally acceptable adjuvants.

DETAILED DESCRIPTION OF THE INVENTION

In the above-described definition of the formula (I), suitable examples of the halogen atoms which may be employed as substituent Y include a fluorine atom, a chlorine atom, a bromine atom and an iodine atom. Suitable examples of the alkyl moiety in the ($C_1$-$C_4$) alkyl groups or ($C_1$-$C_4$) alkoxy groups which may be employed as substituent X, $R_1$ and $R_2$ include a methyl group, an ethyl group, an n-propyl group, an isopropyl group, an n-butyl group, an isobutyl group, a sec-butyl group and a tert-butyl group. Suitable examples of the cations which may be employed as substituent $R_1$ and $R_2$ include an alkali metal ion such as sodium ion and potassium ion, an ammonium ion, and an organic ammonium ion such as dimethyl ammonium ion and diethanol ammonium ion.

Of the compounds of the formula (I), it is particularly preferred for X to be a -$COOR_1$ group wherein $R_1$ is a hydrogen atom, a cation or a ($C_1$-$C_4$) alkyl group, and an

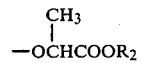

group wherein $R_2$ is a hydrogen atom, a cation, a ($C_1$-$C_4$) alkyl group or a benzyl group, and for Y to be a halogen atom, a nitro group or a cyano group.

The compounds of the present invention of the formula (I) can be produced by the methods described below.

METHOD A

A 2-halo-3-chloro-5-trifluoromethyl pyridine of the formula (II):

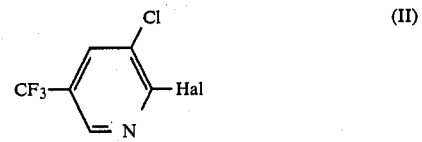

wherein Hal is a halogen atom, and a substituted phenol of the formula (III):

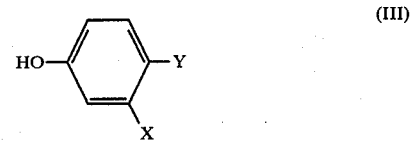

wherein X is a hydrogen atom; a ($C_1$-$C_4$) alkyl group; a ($C_1$-$C_4$) alkoxy group; a -$COOR_1$ group wherein $R_1$ is a hydrogen atom, a cation or a ($C_1$-$C_4$) alkyl group; or an

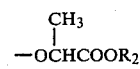

group wherein $R_2$ is a hydrogen atom, a cation, a ($C_1$-$C_4$) alkyl group or a benzyl group; and Y is a halogen atom, a nitro group or a cyano group, are reacted in the presence of an alkaline material at a temperature of 10° to 180° C., preferably 50° to 150° C., for 1 to 20 hours, preferably 1 to 10 hours, to form the compound of the present invention of the formula (I):

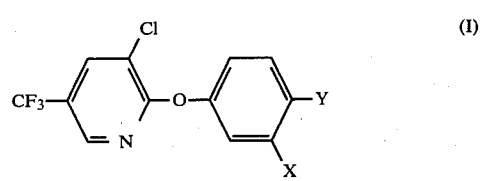

wherein X and Y are the same as defined hereinbefore.

The starting materials described in the above method, i.e. the 2-halo-3-chloro-5-trifluoromethyl pyridine of the formula (II) is described in, for example DT-OS No. 2,812,607, and the substituted phenol of the formula (III) is described in, for example British Patent No. 1,390,295.

Suitable examples of the alkaline materials which can be used in the above described method are alkali metal hydroxides such as sodium hydroxide or potassium hydroxide, and alkali metal carbonates such as sodium carbonate or potassium carbonate. Polar aprotic solvent such as dimethyl sulfoxide, dimethyl formamide, hexamethylphosphoramide or sulfolane can be used in the above described method as a solvent.

Certain compounds of the present invention can be also produced by the following method with industrial advantages.

METHOD B

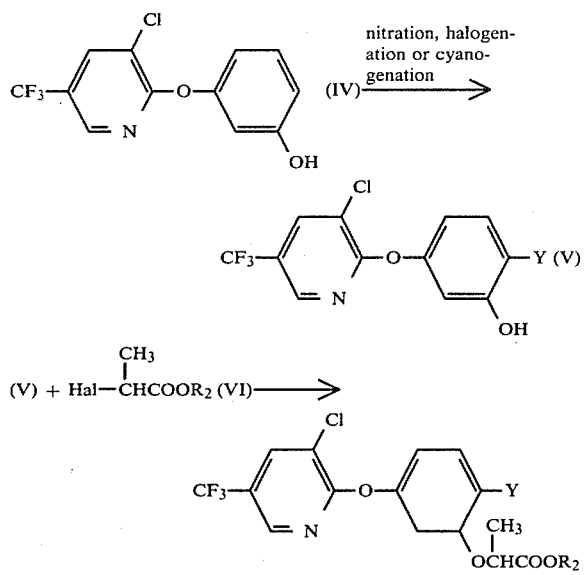

In the reaction formula, Y is a halogen actom, nitro group or cyano group; Hal. is a halogen atom; $R_2$ is a hydrogen atom, a cation, a ($C_1$-$C_4$) alkyl group or benzyl group.

The compound of the formula (IV) can be produced by reacting 2-halo-3-chloro-5-trifluorometyl pyridine of the formula (II) with resorcine by the Method A.

The compound of the formula (VI) is a known compound described in the specification of U.S. Pat. No. 4,046,553, etc.

METHOD C

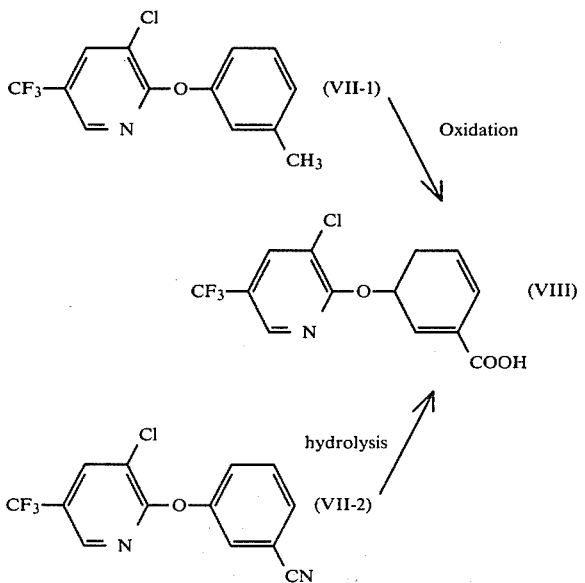

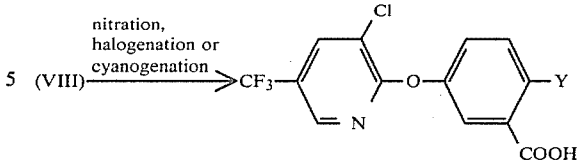

In the reaction formula, Y is a halogen atom, nitro group or cyano group.

The compounds of the formula (VII-1) and VII-2) can be respectively produced by reacting 3-methyl phenol or 3-cyano phenol with 2-halo-3-chloro-5-trifluoromethyl pyridine of the formula (II) by Method A.

Some specific examples of preparing the compounds of this invention are shown below.

PREPARATION EXAMPLE 1

2-(4-chlorophenoxy)-3-chloro-5-trifluoromethyl pyridine

In a falsk, 4.0 g of 2,3-dichloro-5-trifluoromethyl pyridine, 10 ml of dimethyl sulfoxide, 5.1 g of anhydrous potassium carbonate and 2.9 g of p-chlorophenol were charged. The flask was heated in an oil bath at 110° C. to react them with stirring for 2 hours. The completion of the reaction was confirmed by a gas chromatography. The reaction mixture was cooled and poured into suitable amount of water. The reaction product was extracted with methylene chloride and the extracted phase was washed with a diluted sodium hydroxide aqueous solution and then, with water and dried over anhydrous sodium sulfate. Methylene chloride was distilled off under a reduced pressure and the oily residue was distilled to obtain 4.4 g of the object compound having a boiling point of 124°-127° C./2.5 mmHg.

PREPARATION EXAMPLE 2

2-(4-nitrophenoxy)-3-chloro-5- trifluoromethyl pyridine

In a flask, 64 g of 2,3-dichloro-5-trifluoromethyl pyridine, 250 ml of dimethyl sulfoxide, 81.8 g of anhydrous potassium carbonate and 33.4 g of phenol were charged. The flask was heated in an oil bath at 100° C. to react them with stirring for 4 hours. The reaction mixture was poured into suitable amount of water and the reaction product was extracted with methylene chloride. The extracted phase was washed with water, with 5% sodium hydroxide aqueous solution and then, with water and dried over anhydrous sodium sulfate. Methylene chloride was distilled off under a reduced pressure and the residue was distilled to obtain 49 g of 2-phenoxy-3-chloro-5-trifluoromethyl pyridine. The product was mixed with 100 ml of 98% sulfuric acid and the mixture was cooled with ice water. A mixture of 11.3 g of 60% nitric acid and 30 ml of 98% sulfuric acid was added dropwise to the sulfuric acid solution of the reaction product at a temperature of 0° to 10° C. A mild exothermic reaction was performed. After the reaction, the reaction mixture was poured into suitable amount of ice water and neutralized with 10% sodium hydroxide aqueous solution. The reaction product was extracted with methylene chloride. The extracted phase was dried over anhydrous sodium sulfate. Methylene chloride was distilled off under a reduced pressure to obtain 38.5 g of the object compound having a melting point of 90° to 91° C.

PREPARATION EXAMPLE 3

Methyl 2-nitro-5-(3-chloro-5-trifluoromethyl-2-pyridyloxy) benzoate

The process of Preparation Example 2 was repeated except using 51 g of methyl 3-hydroxy benzoate instead of 33.4 g of phenol, to obtain 50 g of methyl 3-(3-chloro-5-trifluoromethyl-2-pyridyloxy) benzoate. Then, 5 g of the resulting compound was mixed with 20 ml of 98% sulfuric acid and the mixture was maintained at a temperature of lower than 5° C. A mixture of 1.4 g of 70% nitric acid and 5 g of 98% sulfuric acid was added dropwise to the reaction mixture. After a completion of the exothermic reaction, the reaction mixture was stirred at room temperature for 30 minutes. In accordance with the process of Preparation Example 2, the extraction, the washing and the drying were carried out to obtain 1.0 g of the object compound having a melting point of 56° to 57° C.

PREPARATION EXAMPLE 4

Sodium 2-nitro-5-(3-chloro-5-trifluoromethyl-2-pyridyloxy) benzoate

Methyl 2-nitro-5-(3-chloro-5-trifluoromethyl-2-pyridyloxy) benzoate was hydrolyzed to obtain 2-nitro-5-(3-chloro-5-trifluoromethyl-2-pyridyloxy) benzoic acid. Then, 350 mg of the product was dissolved in 3 ml of isopropyl alcohol. The solution was admixed with a solution of 40 mg of sodium hydroxide in 1 ml of water. The mixture was stirred at room temperature for 30 minutes. The solvent was distilled off under a reduced pressure to obtain 350 mg of a crude object compound.

PREPARATION EXAMPLE 5

Ethyl 2-[2-bromo-5-(3-chloro-5-trifluoromethyl-2-pyridyloxy) phenoxy] propionate In 150 ml of chloroform, 5.5 g of 2-(3-hydroxyphenoxy)-3-chloro-5-trifluoromethyl pyridine was dissolved and then, 3.5 g of bromine was added dropwise to the solution at a temperature of 10° to 15° C. After the reaction, the reaction product was washed with water, with a sodium bicarbonate aqueous solution, with a saturated sodium thiosulfate solution and then, with water and dried over anhydrous sodium sulfate. Chloroform was distilled off under a reduced pressure and the resulting crystals were washed with hexane and dried to obtain 3.0 g of 2-(3-hydroxy-4-bromophenoxy)-3-chloro-5-trifluoromethyl pyridine having a melting point of 124° to 127° C.

In 30 ml of methyl ethyl ketone, 2.9 g of the resulting product and 1.42 g of ethyl 2-bromopropionate were dissolved and then, 2.2 g of anhydrous potassium carbonate were added. The mixture was refluxed for 3 hours to react them. After the reaction, the solvent was distilled off under a reduced pressure. The residue was poured into suitable amount of water and the product was extracted with methylene chloride. The extracted phase was washed with water and dried over anhydrous sodium sulfate. Methylene chloride was distilled off and 3.5 g of the resulting oily product was adsorbed in a silica gel column and developed and eluted with toluene to obtain 2.4 g of the object compound ($n_D^{15}$ 1.5440).

PREPARATION EXAMPLE 6

Ethyl-2-[2-cyano-5-(3-chloro-5-trifluoromethyl-2-pyridyloxy) phenoxy] propionate A mixture of 1 g of ethyl 2-[2-bromo-5-(3-chloro-5-trifluoromethyl-2-pyridyloxy) phenoxyl] propionate, 0.3 g of cuprous cyanide and 3 ml of dimethylformamide was refluxed for 5 hours to react them. After the reaction, the reaction mixture was poured into suitable amount of water dissolving ferric chloride. The product was extracted with methylene chloride. The extracted solution was washed with water and dried over anhydrous sodium sulfate. The solvent was distilled off under a reduced pressure. The resulting oily product was adsorbed in a silica gel column and developed and eluted with a mixture of n-hexane, toluene and methylene chloride to obtain 0.2 g of the object compound having a boiling point of 163° to 165° C./0.5 mmHg.

PREPARATION EXAMPLE 7

Ethyl 2-[2-nitro-5-(3-chloro-5-trifluoromethyl-2-pyridyloxy) phenoxy] propionate 2,3-Dichloro-5-trifluoromethyl pyridine was condensed with resorcine and the product was nitrated with a mixed acid of nitric acid and sulfuric acid to obtain 2-(3-hydroxy-4-nitrophenoxy)-3-chloro-5-trifluoromethyl pyridine. In 10 ml of methyl ethyl ketone, 1.67 g of the resulting product and 1.09 g of ethyl 2-bromopropionate were dissolved and then, 1.38 g of anhydrous potassium carbonate was admixed. The mixture was refluxed with stirring for 4 hours. After the reaction, a small amount of water was added to the reaction mixture. The solvent was distilled off and the product was extracted with methylene chloride. The extracted phase was washed with water and dried over anhydrous sodium sulfate. Methylene chloride was distilled off. The resulting oily product was adsorbed in a silica gel column and developed and eluted with toluene to obtain 0.8 g of the object compound ($n_D^{15}$ 1.5337).

Typical examples of the compounds of the formula (I) of the present invention are given below:

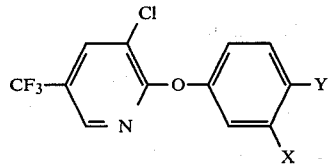

| Compound No. | X | Y | Physical Constant |
|---|---|---|---|
| 1 | H | CN | mp 64°–66° C. |
| 2 | H | NO$_2$ | mp 90°–91° C. |
| 3 | —OCH$_3$ | NO$_2$ | $n_D^{16}$ 1.5680 |
| 4 | —COOCH$_3$ | NO$_2$ | mp 56°–57° C. |
| 5 | —COOH | NO$_2$ | mp 124°–128° C. |
| 6 | —OCHCOOC$_2$H$_5$ with CH$_3$ | NO$_2$ | $n_D^{15}$ 1.5337 |
| 7 | —OCHCOOC$_2$H$_5$ with CH$_3$ | Br | $n_D^{15}$ 1.5440 |
| 8 | —OCHCOOCH$_2$—⟨phenyl⟩ with CH$_3$ | Br | $n_D^{15}$ 1.5646 |

-continued

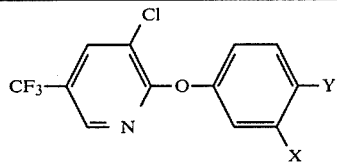

| Compound No. | X | Y | Physical Constant |
|---|---|---|---|
| 9 | CH₃ \| —OCHCOOCH₂—⟨ ⟩ | CN | bp 175°–177° C./ 1.5 mmHg |
| 10 | H | Cl | bp 124°–127° C./ 2.5 mmHg |
| 11 | CH₃ | NO₂ | bp 173°–180° C./ 5 mmHg |
| 12 | —COOC₄H₉(n) | NO₂ | bp 185°–188° C./ 2 mmHg |
| 13 | —COONa | NO₂ | mp 200°–210° C. |
| 14 | CH₃ \| —OCHCOOC₄H₉(n) | NO₂ | bp 168°–172° C./ 1.1mmHg |
| 15 | CH₃ \| —OCHCOOH | Br | mp 115°–118° C. |
| 16 | CH₃ \| —OCHCOOC₂H₅ | CN | bp 163°–165° C./ 0.5 mmHg |
| 17 | —COOK | NO₂ | mp 150°–180° C. |

The compounds having the formula (I) of the present invention have excellent herbicidal effect when they are used as active ingredients in herbicidal compositions as shown in the following Test Examples.

The compounds having the formula (I) wherein X is -COOR₁ group, are remarkably effective for killing noxious weeds without any phytotoxicity to soybean. The compounds having the formula (I) wherein X is

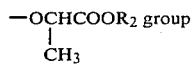

are remarkably effective for killing noxious weeds without any phytotoxicity to corn and wheat.

The compounds of the present invention can be applied by a foliage treatment or a soil treatment to weeds and can be applied to paddy field, up-land farm, orchards, and forests.

The compounds of the present invention can be applied in the form of aqueous solution or aqueous dispersion prepared by dissolving or dispersing the compound in water. The compounds of the present invention can be also used in the form of emulsifiable concentrates, wettable powder, water miscible solution, dusts and granules which are prepared by mixing the compound with an agricultural adjuvant.

Suitable agricultural adjuvants include solid carriers such as diatomaceous earth, calcium hydroxide, calcium carbonate, talc, whitecarbon, kaoline, bentonite, Jeeklite (Trade mark for a zeolite produced by Jeeklite Co.); and solvents such as n-hexane, toluene, xylene, solvent naphtha, ethanol, dioxane, acetone, isophorone methyl isobutyl ketone, dimethylformamide, dimethylsulfoxide and water; and anionic or nonionic surface active agents such as sodium alkylsulfate, sodium alkylbenzene-sulfonate, sodium ligninsulfonate, polyoxyethylene lauryl ether, polyoxyethylene alkyl aryl ether, polyoxyethylene fatty acid ester, polyoxyethylene sorbitan fatty acid ester, etc. These adjuvants can be selected as desired to prepare the herbicidal composition.

The herbicidal compositions usually comprise 1 to 90 wt.%, preferably 1 to 70 wt.% of the active ingredient; 5 to 99 wt.% preferably 25 to 99 wt.% of the carrier or the solvent and 0 to 30 wt.% preferably 1 to 20 wt.% of the surface active agent.

The active ingredient can be combined with other agricultural chemicals such as other herbicides, insecticides, fungicides or fertilizers or soils. In some cases, synergistic effect may be obtained.

Suitable amount of the herbicide of the present invention is depending upon the conditions of weather or soil, form of the composition, time of application, method of application and kinds of weeds, etc. and is usually in a range of 0.1 to 100 g preferably 0.5 to 70 g per are as an active ingredient.

TEST EXAMPLE 1

Each pot of 1/5,000 are (are = 100 m²) was filled with a paddy soil and the soil was supersaturated with water. Seeds of edible barnyard grass were sown in the pot and covered with soil. The barnyard grass was sprout in up-land condition and then it was grown in the flooded condition of a depth of 3 cm. Each aqueous dispersion of each active ingredient diluted with water was poured into the pot at the predetermined ratio when its coleoptile was appeared.

Three weeks after the treatment, the growth conditions of weeds were observed. "Degree of growth control" is shown by 5 ratings as the following standards.
5: Complete growth suppression is found;
4: Remarkable growth suppresion is found;
3: About 60% growth suppression is found;
2: About 30% growth suppresion is found;
1: No apparent difference between treated plants and untreated plants is found.
The result is shown in Table 1.
note: Herbicidal composition; Emulsifiable concentrate prepared by uniformly mixing 20 wt. parts of each active ingredient, 60 wt. parts of xylene and 20 wt. parts of Sorpol 2806 B(Trade name for a mixture of a polyoxyethylene phenyl phenol derivative, a polyoxyethylene alkylaryl ether, a polyoxyethylene sorbitan alkylate and an alkylaryl sulfonate produced by Toho Chemical Co., Ltd.

TABLE 1

| Active ingredient | Degree of growth control | |
|---|---|---|
| | Amount of active ingredient | |
| | 5(g/are) | 2.5(g/are) |
| Compound No. 2 | 5 | 5 |
| Compound No. 4 | 5 | 5 |
| Compound No. 5 | 5 | 5 |
| Compound No. 6 | 5 | 5 |
| Compound No. 8 | 5 | 4–5 |
| Compound No. 9 | 5 | 5 |

TEST EXAMPLE 2

Each pot of 1/3,000 are was filled with an up-land soil. Seeds of barnyard grass were sown in the pot and covered with up-land-soil containing seeds of large crab-grass, Lady's thumb to a depth of about 1 cm.

Two days after the sowing, an aqueous dispersion of each active ingredient diluted with water (the dispersion used in Test Example 1) was sprayed into the pot.

Thirty days after the treatment, the growth condition of weeds were observed. The results are shown in Table 2. "Degree of growth control" is shown by 10 ratings as the following standards.
10: Complete growth suppression is found;
1: No apparent difference between treated plants and untreated plants is found.

TABLE 2

| Active ingredient | Amount of active ingredient (g/are) | Degree of growth control | | |
|---|---|---|---|---|
| | | Barnyard grass | Large crab-grass | Lady's thumb |
| Compound No. 3 | 100 | 10 | 10 | 10 |
| | 50 | 9 | 10 | 10 |
| Compound No. 4 | 100 | 7 | 10 | 10 |
| | 50 | 7 | 10 | 10 |
| Compound No. 6 | 100 | 10 | 10 | 10 |
| | 50 | 9 | 10 | 10 |
| Compound No. 8 | 100 | 5 | 8 | 10 |
| | 50 | 4 | 7 | 8 |
| Compound No. 16 | 100 | 10 | 10 | 10 |
| | 50 | 8 | 10 | 10 |
| Compound No. 1 | 100 | 10 | 10 | 10 |
| | 50 | 10 | 7 | 8 |
| Compound No. 2 | 100 | 10 | 10 | 10 |
| | 50 | 10 | 10 | 10 |
| Compound No. 5 | 100 | 10 | 10 | 10 |
| | 50 | 10 | 10 | 10 |
| Compound No. 11 | 100 | 10 | 10 | 10 |
| | 50 | 10 | 10 | 10 |
| Compound No. 12 | 100 | 10 | 10 | 10 |
| | 50 | 10 | 8 | 10 |
| Compound No. 13 | 100 | 10 | 10 | 10 |
| | 50 | 10 | 10 | 10 |
| Compound No. 14 | 100 | 10 | 10 | 10 |
| | 50 | 9 | 10 | 10 |
| Compound No. 15 | 100 | 9 | 9 | 10 |
| | 50 | 7 | 8 | 10 |

TEST EXAMPLE 3

Each pot of 1/3,000 are was filled with soil to be an up-land culture condition. Seeds of crop plants of soybean, wheat, cotton and corn and weeds of Large crab-grass, Redroot pigweed, Common lambsquarters and Lady's thumb were sown and covered with soil to a depth of about 1 cm.

Three days after the sowing, each aqueous dispersion of each active ingredient diluted with water (the dispersion used in Test Example 1) was sprayed at a ratio of 5 g/are of the active ingredient.

Thirty days after the treatment, the growth condition of the crop plants and weeds was observed and "Degree of growth control" is shown by the rating of Test Example 2. The result is shown in Table 3.

TABLE 3

| Active ingredient | Degree of growth control | | | | | | | |
|---|---|---|---|---|---|---|---|---|
| | Crop plant | | | | Weed | | | |
| | A | B | C | D | E | F | G | H |
| Compound No. 3 | 1 | 1 | 2 | 1 | 6 | 9 | 10 | 6 |
| Compound No. 6 | 1 | 2 | 2 | 1 | 9 | 10 | 10 | 6 |
| Compound No. 16 | 1 | 1 | 2 | 1 | 6 | 10 | 10 | 6 |
| Compound No. 11 | 3 | 2 | 3 | 2 | 9 | 10 | 10 | 10 |
| Compound No. 12 | 1 | 2 | 1 | 1 | 6 | 10 | 10 | 9 |
| Compound No. 14 | 1 | 1 | 2 | 1 | 8 | 10 | 10 | 7 |
| Compound No. 15 | 1 | 1 | 1 | 1 | 6 | 8 | 9 | 6 | note:
A: soybean
B: wheat
C: cotton
D: Corn
E: Large crab-grass
F: Redroot pigweed
G: Common lambsquarters
H: Lady's thumb

TEST EXAMPLE 4

Each pot of 1/5,000 are was filled with soil to be up-land culture condition. Seeds of the crops and weeds shown in Table 4 were sown. At the time of the growth of the plants of unifoliate stage of soybean, two leaf stage of corn, 3 leaf stage of wheat, and two leaf stage of Redroot pigweed, common lambsquarters and Lady's thumb and 2.5 leaf stage of common groundsel, each aqueous dispersion of each active ingredient diluted with 4.5 liter per are was sprayed in foliage treatment.

Twenty five days after the treatment, the growth condition of the crop plants and weeds was observed and "Degree of growth control" is shown by the rating of Test Example 2. The result is shown in Table 4.

TABLE 4

| Active ingredient | Amount of active ingredient (g/are) | Degree of growth control | | | | | |
|---|---|---|---|---|---|---|---|
| | | Crop plant | | | Weed | | |
| | | I | J | K | L | M | N | O |
| Compound No. 13 | 5 | 2 | — | — | 10 | 10 | 10 | 10 |
| Compound No. 15 | 2.5 | — | 2 | 1 | 10 | 10 | 10 | 10 | note:
I: soybean;
J: corn;
K: wheat;
L: Redroot pigweed
M: Common lambsquarters;
N: Lady's thumb;
O: Common groundsel Herbicidal composition, Wettable powder prepared by uniformly mixing each active ingredient with the adjuvant at a ratio of 4:1. The adjuvant was a mixture of 78 wt. parts of Jeeklite, 2 wt. parts of Lavelin S (Trade name for a sodium naphthalene sulfonate-formaldehyde condensate produced by Daiichi Kogyo Seiyaku Co., Ltd.) 5 wt. parts of Sorpol 5039 (Trade name for a sulfate of polyoxyethylene alkylaryl ether produced by Toho Chemical Co., Ltd.) and 15 wt. parts of Carplex (Trade name for whitecarbon (SiO$_2$.nH$_2$O) produced by Shionogi Seiyaku Co., Ltd.)

Typical composition will be illustrated.

| Composition 1: | | |
|---|---|---|
| (1) | Ethyl 2-[2-nitro-5-(3-chloro-5-trifluoromethyl-2-pyridyloxy)phenoxy] propionate | 20 wt. parts |
| (2) | Xylene | 60 wt. parts |
| (3) | Sorpol 2806B | 20 wt. parts |

The components (1)-(3) were uniformly mixed to give an emulsifiable concentrate.

| Composition 2: | |
|---|---|
| (1) Jeeklite | 78 wt. parts |
| (2) Lavelin S | 2 wt. parts |
| (3) Sorpol 5039 | 5 wt. parts |
| (4) Carplex | 15 wt. parts |

The mixture of these components (1)-(4) was mixed with potassium 2-nitro-5-(3-chloro-5-trifluoromethyl-2-pyridyloxy) benzoate at a ratio of 4:1 by weight to give a wettable powder.

| Composition 3: | |
|---|---|
| (1) 2-[2-nitro-5-(3-chloro-5-trifluoromethyl-2-pyridyloxy)phenoxy] propionic acid | 20 wt. parts |
| (2) Jeeklite | 75 wt. parts |
| (3) Sodium lignin sulfonate | 3 wt. parts |
| (4) Lavelin S | 2 wt. parts |

The components (1)-(4) were uniformly mixed to give a wettable powder.

| Composition 4: | |
|---|---|
| (1) Sodium 2-nitro-5-(3-chloro-5-trifluoromethyl-2-pyridloxy) benzoate | 20 wt. parts |
| (2) Water | 80 wt. parts |

The component (1) was dissolved in water to give a solution.

| Composition 5: | |
|---|---|
| (1) Bentonite | 58 wt. parts |
| (2) Jeeklite | 30 wt. parts |
| (3) Sodium lignin sulfonate | 5 wt. parts |

The components (1)-(3) were mixed and granulated. A solution of 7 wt. parts of methyl 2-nitro-5-(3-chloro-5-trifluoromethyl-2-pyridyloxy) benzoate in acetone was sprayed on the granulated components to give a granulate.

What is claimed is:

1. A compound having the formula (I):

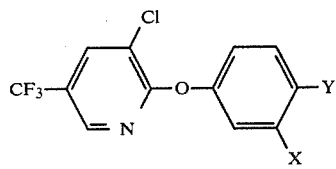

wherein X is hydrogen; $(C_1-C_4)$ alkyl; $(C_1-C_4)$ alkoxy; $-COOR_1$ wherein $R_1$ is hydrogen, a cation or $(C_1-C_4)$ alkyl; or

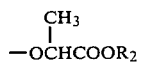

wherein $R_2$ is hydrogen, cation, $(C_1-C_4)$ alkyl or benzyl; and Y is halogen, nitro or cyano.

2. The compound of claim 1, wherein X is $-COOR_1$ wherein $R_1$ is hydrogen atom, a cation or $(C_1-C_4)$ alkyl and Y is halogen, nitro or cyano.

3. The compound of claim 1, wherein X is $-COOR_1$ wherein $R_1$ is a cation, and Y is nitro or cyano.

4. The compound of claim 1, wherein X is

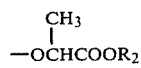

wherein $R_2$ is hydrogen, a cation, $(C_1-C_4)$ alkyl or benzyl, and Y is halogen nitro group or cyano.

5. The compound of claim 1, wherein X is

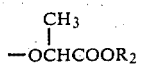

wherein $R_2$ is $(C_1-C_4)$ alkyl, and Y is nitro or cyano.

6. The compound of claim 1, wherein the compound is sodium 2-nitro-5-(3-chloro-5-trifluoromethyl-2-pyridyloxy) benzoate.

7. The compound of claim 1, wherein the compound is methyl 2-nitro-5-(3-chloro-5-trifluoromethyl-2-pyridyloxy) benzoate.

8. The compound of claim 1, wherein the compound is ethyl α-[2-nitro-5-(3-chloro-5-trifluoromethyl-2-pyridyloxy) phenoxy] propionate.

9. The compound of claim 1, wherein the compound is n-butyl α-[2-nitro-5-(3-chloro-5-trifluoromethyl-2-pyridyloxy) phenoxy] propionate.

10. The compound of claim 1, wherein the compound is ethyl α-[2-cyano-5-(3-chloro-5-trifluoromethyl-2-pyridyloxy) phenoxy] propionate.

11. A herbicidal composition comprising from 1 to 90 weight percent of at least one compound having the formula (I)

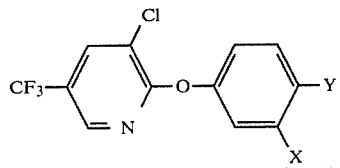

wherein X is hydrogen; $(C_1-C_4)$ alkyl; $(C_1-C_4)$ alkoxy; $-COOR_1$ wherein $R_1$ is hydrogen, a cation or $(C_1-C_4)$ alkyl; or

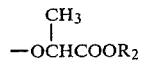

wherein $R_2$ is hydrogen, a cation, $(C_1-C_4)$ alkyl or benzyl; and Y is halogen, nitro or cyano, as an active ingredient, and agriculturally acceptable adjuvants.

12. The herbicidal composition of claim 11, wherein X is $-COOR_1$ wherein $R_1$ is hydrogen, a cation or $(C_1-C_4)$ alkyl, and Y is halogen, nitro or cyano.

13. The herbicidal composition of claim 11, wherein X is $-COOR_1$ wherein $R_1$ is a cation, and Y is nitro or cyano.

14. The herbicidal composition of claim 11, wherein X is

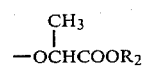

wherein $R_2$ is hydrogen, a cation, $(C_1-C_4)$ alkyl or benzyl, and Y is halogen, nitro or cyano.

15. The herbicidal composition of claim 11, wherein X is

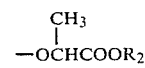

wherein $R_2$ is $(C_1-C_4)$ alkyl, and Y is nitro or cyano.

16. The herbicidal composition of claim 11, wherein the compound is sodium 2-nitro-5-(3-chloro-5-trifluoromethyl-2-pyridyloxy) benzoate.

17. The herbicidal composition of claim 11, wherein the compound is methyl 2-nitro-5-(3-chloro-5-trifluoromethyl-2-pyridyloxy) benzoate.

18. The herbicidal composition of claim 11, wherein the compound is ethyl α-[2-nitro-5-(3-chloro-5trifluoromethyl-2-pyridyloxy) phenoxy] propionate.

19. The herbicidal composition of claim 11, wherein the compound is n-butyl α-[2-nitro-5-(3-chloro-5-trifluoromethyl-2-pyridyloxy) phenoxy] propionate.

20. The herbicidal composition of claim 11, wherein the compound is ethyl α-[2-cyano-5-(3-chloro-5-trifluoromethyl-2-pyridyloxy) phenoxy] propionate.

* * * * *